United States Patent [19]
De Lacharriere et al.

[11] Patent Number: 5,869,068
[45] Date of Patent: Feb. 9, 1999

[54] COMPOSITIONS AND METHODS FOR TREATING WRINKLES AND/OR FINE LINES OF THE SKIN

[75] Inventors: Olivier De Lacharriere, Paris; Lionel Breton, Versailles, both of France

[73] Assignee: L'Oreal, Paris, France

[21] Appl. No.: 538,119

[22] Filed: Oct. 2, 1995

[30] Foreign Application Priority Data

Sep. 30, 1994 [FR] France .................................. 94 11742

[51] Int. Cl.$^6$ ...................................................... A61K 7/48
[52] U.S. Cl. .......................... 424/401; 514/844; 514/846; 514/944
[58] Field of Search ............................ 424/401; 514/844, 514/846, 944

[56] References Cited

U.S. PATENT DOCUMENTS 5,385,938  1/1995  Yu et al. ................................. 514/557

FOREIGN PATENT DOCUMENTS

| 0 466 236 | 1/1992 | European Pat. Off. . |
| 2 633 515 | 1/1990 | France . |
| 2 679 788 | 2/1993 | France . |
| 2 142 237 | 1/1985 | United Kingdom . |
| 86/06275 | 11/1986 | WIPO . |

OTHER PUBLICATIONS

Parfums–Cosmetique–Aromes, No. 47, pp. 55–56, 1982, T. Suzuki, et al., "Emulsions a Gouttelettes Secondaires".

Journal of Dispersion Science and Technology, vol. 5, No. 2, pp. 119–141, 1984, T. Suzuki, et al., "Secondary Droplet Emulsion: Mechanism and Effects of Liquid Crystal Formation in O/W Emulsion".

J. Appl. Cosmetol., vol. 12, No. 1, pp. 1–9, Jan.–Mar. 1994, P. Morganti, et al., "Topical Gelatin–Glycine and Alpha Hydroxy Acids for Photoaged Skin".

STN International, Karlsruhe File Chemical Abstracts, AN–103:59105, RO–B–85674, Nov. 30, 1984.

Patent Abstracts of Japan, vol. 17, No. 342 (C–1076), Jun. 29, 1993, JP–A–05 043 448, Feb. 23, 1993.

Patent Abstracts of Japan, vol. 10, No. 31 (C–327), Feb. 6, 1986, JP–A–60 184 005, Sep. 19, 1985.

STN International, Karlsruhe Chemical Abstracts, AN–101:60150, JP–A–59 053 409, Mar. 28, 1984.

J. Dermatol. Surg. Oncol., vol. 18, No. 1, pp. 17–21, 1992, J.D.A. Carruthers, et al., "Treatment of Glabellar Frown Lines with *C. botulinum*–A Exotoxin".

*Primary Examiner*—Jyothsna Venkat
*Attorney, Agent, or Firm*—Oblon, Spivak, McClelland, Maier & Neustadt, P.C.

[57] ABSTRACT

Compositions which contain an agonist substance of one or a number of receptors associated with a chlorine channel are useful for slackening and/or relaxing cutaneous tissue, and in particular for the purpose of treating wrinkles and fine lines of the skin. Such compositions can be administered topically or by injection. Preferred agonists include glycine, serine, taurine, β-alanine, N-(benzyloxycarbonyl)glycine (Z-glycine), gamma-aminobutyric acid (GABA), isoguvacine, isonipecotic acid, 4,5,6,7-tetrahydroisoxazolo [5,4-c]pyrid-3(2H)-one, benzodiazepines, steroids, and barbiturates. The composition can additionally contain a retinoid and/or a hydroxy acid.

34 Claims, No Drawings

COMPOSITIONS AND METHODS FOR TREATING WRINKLES AND/OR FINE LINES OF THE SKIN

BACKGROUND OF THE INVENTION

Field of the Invention

The present invention relates to the use of substances which are agonists of a receptor associated with a chlorine channel in a cosmetic and/or dermatological composition, in particular for the purpose of treating wrinkles and fine lines of the skin, and to cosmetic and/or dermatological compositions which contain such a substance.

Discussion of the Background

Women, and indeed even men, are currently inclined to wish to appear young for as long as possible and consequently are looking to soften the signs of ageing of the skin, which are reflected in particular by wrinkles and fine lines. In this respect, advertising and fashion present products intended to retain a radiant and wrinkle-free skin, these being the signs of young skin, for as long as possible, all the more so since physical appearance has an effect on mental attitude and/or on morale. It is consequently important to feel physically and spiritually young.

Until now, wrinkles and fine lines have been treated using cosmetic products containing active agents which act on the skin, for example by moisturizing it or by improving its cell renewal or alternatively by promoting the synthesis of collagen of which the cutaneous tissue is composed. However, to date, it is not known to act on wrinkles by involving the muscle components present in the skin.

It is known that the platysma muscles of the face are under the control of the motor nerve afferent activity of the facial nerve and that, moreover, the interlobular septa of the hypoderm contain within them fibers which constitute a striated muscle tissue (panniculus carnosus). Moreover, it is also known that a subpopulation of fibroblasts of the dermis, known as myofibroblasts, has characteristics in common with the muscle tissue.

The Applicants have observed, in certain pathological and therapeutic situations, the role played, as regards the wrinkles of the face, by the nerves controlling all this muscle tissue. Thus, in attacks on the facial nerve, in which transmission of the nerve impulse is interrupted and/or weakened, a paralysis of the muscles of the face is witnessed in the area of innervation. This facial paralysis is reflected, among other clinical indications, by an alleviation in, indeed disappearance of, the wrinkles.

On the other hand, in muscle hypercontraction conditions of the face, the Applicants have observed an accentuation in the wrinkles of the face. Moreover, an accentuation in the wrinkles of the face has also been observed in muscle hypertonia conditions of Parkinson's disease and side-effects induced by neuroleptics.

Moreover, it has been shown that botulinus toxin, originally used for treating spasms, could have an effect on muscle spasticity conditions (see A. Blitzer et al., Arch. Otolaryngol. Head Neck Surg., vol 119, pages 1018 to 1022 (1993)) and on the wrinkles of the glabella, which are intersuperciliary wrinkles (see J. D. Carruters et al., J. Dermatol. Sura. Oncol., vol. 18, pages 17 to 21 (1992)). It is consequently possible, by pharmacological action, to have an effect on the nerve component of wrinkles. Botulinus toxin acts directly at the level of the neuro-muscular junction by blocking the action of acetylcholine on muscular tenseness.

The junction between a nerve and a muscle constitutes the myoneural endplate, before which is found the afferent nerve route known as the motor neuron. Moreover, the cell membranes of each nerve fiber contain many ionic channels, and in particular chlorine channels, capable of allowing the corresponding element to pass through in the ionic form, and, in the case of chlorine channels, in the chloride form. Neuronal receptors are associated with these channels. The neuronal receptors associated with the chlorine channels are in particular receptors for glycine (glycine-strychnine sensitive receptors) and receptors for GABA ($GABA_A$ receptors).

Moreover, it is known that, in the central nervous system, it is possible to decrease the excitability of the neuron by various pharmacological agents which have an effect on the glycine-strychnine sensitive receptors or on the $GABA_A$ receptors of the central nervous system (see W. Sieghart, Trends in Pharmacological Science, vol. 131, pages 446 to 450 (December 1992)). Activation of these receptors opens the chlorine channels and leads to the entry of chloride ions, which results in an increase in the chloride ions in the cells of the nerve fiber and thus to hyperpolarization of the neurons, which consequently become less excitable.

On the other hand, in the neuromuscular junction, a decrease in excitability of the motor neuron leads to a lessened stimulation of the muscle fiber, thus causing it to slacken.

However, to date no completely suitable compositions or methods are available for treating wrinkles and/or fine lines of the skin. Thus, there remains a need for methods and compositions effective for treating wrinkles and/or fine lines of the skin.

SUMMARY OF THE INVENTION

Accordingly, it is one object of the present invention to provide novel compositions for treating wrinkles and/or fine lines of the skin.

It is another object of the present invention to provide novel methods for treating wrinkles and/or fine lines of the skin.

These and other objects, which will become apparent during the following detailed description, have been achieved by the inventors' discovery that contractile muscle fibers, which are under the direct control of the neuromotor impulse, play an essential role in the pathogenesis of wrinkles and that suppression of the neuromotor impulse alleviates not only wrinkles but also fine lines and also has a "smoothing" effect on the cutaneous microrelief. It has also been found that cutaneous tissues contain receptors associated with chlorine channels, something which, until now, had not been envisaged. It has thus been found that it is possible to act on these channels in order to slacken or relax these tissues and thus to lessen wrinkles and fine lines.

Until now, a connection between the chlorine channels of nerve fibers of the peripheral cutaneous nervous system and wrinkles had never been established, nor had it been found that it was possible to treat wrinkles by acting on chlorine channels by activation of the receptors which are found in or in the neighborhood of these channels. Substances which can activate the receptors of chlorine channels and thus lead to the entry of chloride into cells are known as agonist substances.

Consequently, the present invention provides topical cosmetic or dermatological compositions, which contain at least one agonist substance of at least one receptor associated with at least one chlorine channel present in cutaneous tissue except glycine and gamma-aminobutyric acid for relaxing and/or slackening cutaneous tissue.

In another aspect, the present invention provides injectable cosmetic or dermatological compositions, for the purpose of lessening wrinkles and/or fine lines, which contain at least one agonist substance of at least one receptor associated with at least one chlorine channel present in cutaneous tissue for relaxing and/or slackening cutaneous tissue. In this context, the term "injectable" means suitable for injection into tissue, and in particular in wrinkles.

The present invention further provides injectable or topical cosmetic or dermatological compositions, which contain at least one agonist substance of at least one receptor associated with at least one chlorine channel of at least one cutaneous afferent nerve pathway for relaxing and/or slackening cutaneous tissue.

The present invention additionally provides topical cosmetic or dermatological compositions for the purpose of lessening wrinkles and/or fine lines which contain at least one agonist substance of at least one receptor associated with at least one chlorine channel of at least one cutaneous afferent nerve pathway, except glycine and gamma-butyric acid, for relaxing and/or slackening cutaneous tissue.

The compositions containing the agonist according to the present invention can be applied topically or by subcutaneous and/or intradermal and/or "intrawrinkle" injection.

Another aspect of the present invention is a method for the cosmetic treatment of wrinkles and/or fine lines in humans by injecting a composition containing at least one agonist substance of at least one receptor associated with at least one chlorine channel present in cutaneous tissue.

DETAILED DESCRIPTION OF THE PREFERRED EMBODIMENTS

A number of receptors associated with the chlorine channel exist. They concern in particular glycine strychnine sensitive receptors and $GABA_A$ receptors, the latter themselves containing a number of subunits comprising the GABA site, the benzodiazepine site, a type of steroid site and the barbiturates site. All the substances which act as agonists of these receptors or sites can be used for slackening or relaxing cutaneous tissues in accordance with the present invention.

For a substance to be recognized as an agonist of a receptor of the chlorine channel, it must exhibit the following two characteristics:

(i) to be able to be bound selectively to at least one of the various receptors associated with the chlorine channel; and (ii) to show a relaxation effect on a contracted muscle tissue.

The first characteristic, which consists of the possibility of being bound to a receptor associated with a chlorine channel, does not make it possible to distinguish an agonist activity from an antagonist activity but it does make it possible to define a potential affinity for the receptor.

The second characteristic makes it possible to select the agonists. The agonist activity of the substance under study can be demonstrated by the relaxation effect which it produces on a muscle tissue which has been contracted beforehand by a chlorine channel antagonist substance. Substances known as chlorine channel antagonists can be chosen as such and in particular include the following substances: bicuculline, strychnine, tert-butylbicyclophosphorothionate and picrotoxin.

Mention may be made, as agonist substances, which can be used in the present invention for activating glycine-strychnine sensitive receptors, of glycine, serine, taurine, β-alanine, and N-(benzyloxycarbonyl)glycine or (Z-glycine).

Mention may be made, as agonist substances, which can be used in the invention for activating $GABA_A$ receptors, of gamma-aminobutyric acid (GABA), isoguvacine, isonipecotic acid, 4,5,6,7-tetrahydroisoxazolo[5,4-c]pyrid-3(2H)-one (THIP), benzodiazepines such as nitrazepam (1,3-dihydro-7-nitro-5-phenyl-2H-1,4-benzodiazepin-2-one), diazepam (7-chloro-1,3-dihydro-1-methyl-5-phenyl-2H-1,4-benzodiazepin-2-one), flunitrazepam (5-(2-fluorophenyl)-1,3-dihydro-1-methyl-7-nitro-2H-1,4-benzodiazepin-2-one) or oxazepam (7-chloro-1,3-dihydro-3-hydroxy-5-phenyl-2H-1,4-benzodiazepin-2-one), certain steroids such as alfaxalone (3-hydroxypregnane-11,20-dione) or barbiturates such as barbital (5,5-diethylbarbituric acid), pentobarbital (5-ethyl-5-(1-methylbutyl)barbituric acid) or phenobarbital (5-ethyl-5-phenylbarbituric acid), and their salts.

It is certainly known to use GABA and glycine in combination with other active agents for combating ageing of the skin but, until now, their action in relaxing and slackening cutaneous tissues for the purpose of treating wrinkles was not known. The generally known actions are inhibition of elastase, the effect on collagen, and cell renewal.

Indeed, it is known in the state of the art to use amino acids as moisturizing agents for the purpose of improving the condition of the skin. In particular, combinations of amino acids such as glycine, taurine or β-alanine in the form of peptide mixtures have been used in cosmetic compositions intended for treating the ageing of the skin. Thus, FR-A-2,546,164 discloses the elastase-inhibiting properties of lipopeptides which prevent deterioration of elastin fibers in the skin, which makes them antiwrinkle active agents. Moreover, U.S. Pat. No. 5,198,465 discloses that amino acids prevent deficiencies in the synthesis of collagen, which consequently makes it possible to prevent ageing of the skin.

In addition, JP-A-05043448 discloses that the combination of GABA and of diisopropylamine facilitates renewal of the skin and thus prevents cutaneous ageing.

In the compositions according to the present invention, the agonist of a receptor associated with the chlorine channel is preferably used in an amount ranging from 0.00001 to 20% by weight, based on the total weight of the composition, and in particular in an amount ranging from 0.01 to 10% by weight, based on the total weight of the composition.

The compositions according to the present invention can be provided in all the pharmaceutical dosage forms normally used for a topical or injectable application.

The amounts of the various constituents of the compositions according to the present invention are those conventionally used in the fields under consideration and are appropriate to their pharmaceutical dosage form.

For topical application, the compositions of the present invention comprise a medium compatible with skin. These compositions can be provided in particular in the form of aqueous, alcoholic or aqueous/alcoholic solutions, of gels, of water-in-oil or oil-in-water emulsions having the appearance of a cream or of a gel, of microemulsions or of aerosols or alternatively in the form of vesicular dispersions containing ionic and/or nonionic lipids. These pharmaceutical dosage forms are prepared according to the conventional methods in the fields under consideration.

The present compositions for topical application can constitute in particular a cosmetic or dermatological protection, treatment or care composition for the face, for the neck, for the hands or for the body (for example day creams, night creams, sun creams or oils or body milks), a make-up composition (for example foundation cream), or an artificial tanning composition.

When the composition of the present invention is an emulsion, the proportion of fatty substance which it contains can range from 5% to 80% by weight, and preferably from 5% to 50% by weight, based on the total weight of the composition. The fatty substances and the emulsifiers used in the composition in the emulsion form are chosen from those conventionally used in the cosmetic or dermatological field.

Mention may be made, as fatty substances which can be used in the present invention, of mineral oils (paraffin), vegetable oils (karite butter liquid fraction) and their hydrogenated derivatives, animal oils, synthetic oils (perhydrosqualene), silicone oils (dimethylpolysiloxane), and fluorinated oils. Mention may also be made, as other fatty substances, of fatty alcohols (cetyl alcohol or stearyl alcohol), fatty acids (stearic acid), and waxes.

The emulsifiers can be present in the present compositions in a proportion ranging from 0.3% to 30% by weight, and preferably from 0.5 to 30% by weight, based on the total weight of the composition.

In a conventional way, the cosmetic or dermatological compositions of the present invention can also contain adjuvants which are typical in the corresponding fields, such as hydrophilic or lipophilic gelling agents, preservatives, antioxidants, solvents, fragrances, fillers, screening agents, and colorants. Moreover, these compositions can contain hydrophilic or lipophilic active agents. The amounts of these various adjuvants or active agents are those conventionally used in the cosmetics or dermatological field and, for example, from 0.01% to 20% of the total weight of the composition. These adjuvants or these active agents, depending on their nature, can be introduced into the fatty phase, into the aqueous phase and/or into lipid vesicles.

Mention may especially be made, among the active agents which the compositions of the invention can contain, of active agents having an effect on the treatment of wrinkles or of fine lines and in particular of keratolytic active agents. The term "keratolytic active agent" is understood to mean an active agent having desquamative, exfoliative or scrubbing properties or an active agent capable of softening the corneal layer.

Mention may in particular be made, among these active agents having an effect on the treatment of wrinkles or fine lines which the compositions of the invention can contain, of hydroxy acids and retinoids.

The hydroxy acids can be, for example, α-hydroxy acids or β-hydroxy acids, which can be linear, branched or cyclic and saturated or unsaturated. The hydrogen atoms of the carbon chain can, in addition, be substituted by halogens or halogenated, alkyl, acyl, acyloxy, alkoxycarbonyl or alkoxy radicals having from 2 to 18 carbon atoms.

The hydroxy acids which can be used are in particular glycolic, lactic, malic, tartaric, citric, 2-hydroxyalkanoic, mandelic, and salicylic acids, and their acyl derivatives, such as 5-n-octanoylsalicylic acid, 5-n-dodecanoylsalicylic acid, 5-n-decanoylsalicylic acid, 5-n-octylsalicylic acid, 5-or 4-n-heptyloxysalicylic acid or 2-hydroxy-3-methylbenzoic acid, or alternatively their alkoxy derivatives such as 2-hydroxy-3-methoxybenzoic acid.

The retinoids can be in particular retinoic acid (all trans or 13-cis) and its derivatives, retinol (vitamin A) and its esters such as retinol palmitate, retinol acetate, and retinol propionate, and their salts.

These active agents can be used in particular at concentrations ranging from 0.0001% to 5% by weight based on the total weight of the composition.

When the compositions of the present invention are intended to be injected, they can be provided in the form of solutions containing the excipients commonly used for injections and for example in the form of an isotonic sodium chloride solution.

Other features of the invention will become apparent in the course of the following descriptions of exemplary embodiments which are given for illustration of the invention and are not intended to be limiting thereof.

EXAMPLES

The amounts indicated in the following Examples are percentages by weight. The term "qsp for 100%" means that that ingredient is present in an amount sufficient to make the total amount of all ingredients equal 100% by weight.

Example 1

Care lotion for the face.

| | |
|---|---|
| Z-Glycine | 8% |
| Antioxidant | 0.05% |
| Preservative | 0.3% |
| Ethanol (solvent) | 8% |
| Water | qsp for 100% |

The lotion obtained has an effect on wrinkles during repeated use (twice daily applications for one month).

Example 2

Gel for caring for the face.

| | |
|---|---|
| Z-Glycine | 5% |
| Hydroxypropylcellulose (Klucel H sold by the company Hercules) (gelling agent) | 1% |
| Preservative | 0.3% |
| Ethanol (solvent) | 15% |
| Antioxidant | 0.05% |
| Water | qsp for 100% |

The gel obtained has an effect on wrinkles. It can be applied daily, morning and evening, for one month.

Example 3

Care cream for the face (oil-in-water emulsion).

| | |
|---|---|
| Flunitrazepam | 0.1% |
| Glyceryl stearate (emulsifier) | 2% |
| Polysorbate 60 (Tween 60 sold by the company ICI) (emulsifier) | 1% |
| Stearic acid | 1.4% |
| Triethanolamine (neutralizing agent) | 0.7% |
| Carbomer (Carbopol 940 sold by the company Goodrich) | 0.4% |
| Karite butter liquid fraction | 12% |
| Perhydrosqualene | 12% |
| Preservative | 0.3% |
| Fragrance | 0.5% |
| Antioxidant | 0.05% |
| Water | qsp for 100% |

A white oily cream is obtained which has an effect on wrinkles and fine lines and which can be applied daily.

Example 4
Care cream for the face (oil-in-water emulsion).

| | |
|---|---|
| Flunitrazepam | 0.2% |
| Glycercyl mono- and distearate | 2% |
| Cetyl alcohol | 1.5% |
| Cetylstearyl alcohol/cetylstearyl alcohol oxyethylenated 33 EO | 7% |
| Dimethylpolysiloxane | 1.5% |
| Liquid paraffin | 17.5% |
| Preservative | 0.3% |
| Fragrance | 0.5% |
| Glycerol | 12.5% |
| Water | qsp for 100% |

This application is based on French Patent Application 94-11742 filed on Sep. 30, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for relaxing or slackening cutaneous tissue, comprising topically applying a cutaneous tissue relaxing or slackening effective amount of at least one agonist substance of at least one receptor associated with at least one chlorine channel present in cutaneous tissue, wherein the agonist substance is selected from the group consisting of serine, taurine, β-alanine, N-(benzyloxycarbonyl)glycine, isoguvacine, isonipecotic acid, 4,5,6,7-tetrahydroisoxazolopyrid-3 (2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

2. The method of claim 1, wherein said agonist substance activates a glycine-strychnine sensitive receptor and is selected from the group consisting of serine, taurine, β-alanine, and N-(benzyloxycarbonyl)glycine.

3. The method of claim 1, wherein said agonist substance is applied in a composition in an amount ranging from 0.00001 to 20% by weight, based on the total weight of said composition.

4. The method of claim 3, wherein said agonist substance is present in said composition in an amount ranging from 0.01 to 10% by weight, based on the total weight of said composition.

5. The method of claim 3, wherein said composition further comprises at least one of a hydroxy acid and a retinoid.

6. The method of claim 5, wherein said hydroxy acid is selected from the group consisting of α-hydroxy acids and β-hydroxy acids, which can be linear, branched or cyclic and saturated or unsaturated.

7. The method of claim 5, wherein said retinoid is selected from the group consisting of retinoic acid, retinol and retinol esters.

8. A method for lessening wrinkles or fine lines, by relaxing or slackening cutaneous tissue comprising topically applying a wrinkle or fine line lessening effective amount of at least one agonist substance of at least one receptor associated with at least one chlorine channel of at least one cutaneous afferent nerve pathway, wherein the agonist substance is selected from the group consisting of serine, taurine, β-alanine, N-(benzyloxycarbonyl)glycine, isoguvacine, isonipecotic acid, 4,5,6,7-tetrahydroisoxazolo-[5,4-c]pyrid-3(2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

9. The method of claim 8, wherein said agonist substance activates a glycine-strychnine sensitive receptor and is selected from the group consisting of serine, taurine, β-alanine, and N-(benzyloxycarbonyl)glycine.

10. The method of claim 8, wherein said agonist substance is applied in a composition in an amount ranging from 0.00001 to 20% by weight, based on the total weight of said composition.

11. The method of claim 10, wherein said agonist substance is present in said composition in an amount ranging from 0.01 to 10% by weight, based on the total weight of said composition.

12. The method of claim 10, wherein said composition further comprises at least one of a hydroxy acid or a retinoid.

13. The method of claim 12, wherein said hydroxy acid is selected from the group consisting of α-hydroxy acids and β-hydroxy acids, which can be linear, branched or cyclic and saturated or unsaturated.

14. The method of claim 12, wherein said retinoid is selected from the group consisting of retinoic acid, retinol and retinol esters.

15. A method for lessening wrinkles or fine lines, comprising administering by injection a cosmetic or dermatological composition, said composition comprising at least one agonist substance of at least one receptor associated with at least one chlorine channel present in cutaneous tissue, wherein the agonist substance is selected from the group consisting of serine, taurine, β-alanine, N-(benzyloxycarbonyl)glycine, isoguvacine,isonipecotic acid, 4,5,6,7-tetrahydroisoxazolopyrid-3(2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin 2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

16. The method of claim 15, wherein said agonist substance activates a glycine-strychnine sensitive receptor and is selected from the group consisting of serine, taurine, β-alanine, and N-(benzyloxycarbonyl)glycine.

17. The method of claim 15, wherein said agonist substance is present in said composition in an amount ranging from 0.00001 to 20% by weight, based on the total weight of said composition.

18. The method of claim 15, wherein said agonist substance is present in said composition in an amount ranging from 0.01 to 10% by weight, based on the total weight of said composition.

19. The method of claim 15, wherein said composition further comprises at least one of a hydroxy acid or a retinoid.

20. The method of claim 19, wherein said hydroxy acid is selected from the group consisting of α-hydroxy acids and β-hydroxy acids, which can be linear, branched or cyclic and saturated or unsaturated.

21. The method of claim 19, wherein said retinoid is selected from the group consisting of retinoic acid, retinol and retinol esters.

22. A method for relaxing or slackening cutaneous tissue, comprising administering by injection a cosmetic or dermatological composition, said composition comprising at least one agonist substance of at least one receptor associated with at least one chlorine channel of at least one cutaneous afferent nerve pathway, wherein the agonist substance is selected from the group consisting of serine, taurine, β-alanine, N-(benzyloxycarbonyl)glycine, isoguvacine, isonipecotic acid, 4,5,6,7-tetrahydroisoxazolo[5,4-c]pyrid-3 (2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

23. The method of claim 22, wherein said agonist substance activates a glycine-strychnine sensitive receptor and is selected from the group consisting of serine, taurine, β-alanine, and N-(benzyloxycarbonyl)glycine.

24. The method of claim 22, wherein said agonist substance is present in said composition in an amount ranging from 0.00001 to 20% by weight, based on the total weight of said composition.

25. The method of claim 22, wherein said agonist substance is present in said composition in an amount ranging from 0.01 to 10% by weight, based on the total weight of said composition.

26. The method of claim 22, wherein said composition further comprises at least one of a hydroxy acid and a retinoid.

27. The method of claim 26, wherein said hydroxy acid is selected from the group consisting of α-hydroxy acids and β-hydroxy acids, which can be linear, branched or cyclic and saturated or unsaturated.

28. The method of claim 26, wherein said retinoid is selected from the group consisting of retinoic acid, retinol and retinol esters.

29. A method for the cosmetic treatment of wrinkles or fine lines in humans, comprising injecting a composition comprising at least one agonist substance of at least one receptor associated with at least one chlorine channel present in cutaneous tissue, wherein the agonist substance is selected from the group consisting of serine, taurine, β-alanine, N-(benzyloxycarbonyl)glycine, isoguvacine, isonipecotic acid, 4,5,6,7-tetrahydroisoxazolo[5,4-c]pyrid-3 (2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

30. The method of claim 1, wherein said agonist substance activates a $GABA_A$ receptor and is selected from the group consisting of isoguvacine, isonipecotic acid, 4,5,6,7-tetrahydroisoxazolo[5,4-c]pyrid-3(2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3hydroxypregnane-11,20-dione, 5,5-diethylbarbituric acid, 5-ethyl-5-(1-methylbutyl)barbituric acid, 5-ethyl-5-phenylbarbituric acid, and their salts.

31. The method of claim 8, wherein said agonist substance activates a $GABA_A$ receptor and is selected from the group consisting of isoguvacine, isonipecotic acid, 4,5,6,7-tetrahydroisoxazolo[5,4-c]pyrid-3(2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

32. The method of claim 15, wherein said agonist substance activates a $GABA_A$ receptor and is selected from the group consisting of gamma-aminobutyric acid, isoguvacine, isonipecotic acid, 4,5,6,7-tetrahydroisoxazolo[5,4-c]pyrid-3 (2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-fluorophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxypregnane-11,20-dione, 5,5-diethylbarbituric acid, 5-ethyl-5-(1-methylbutyl)barbituric acid, 5-ethyl-5-phenylbarbituric acid, and their salts.

33. The method of claim 22, wherein said agonist substance activates a $GABA_A$ receptor and is selected from the group consisting of gamma-aminobutyric acid, isoguvacine, isonipecotic acid 4,5,6,7- tetrahydroisoxazolo pyrid-3(2H)-one, 1,3-dihydro-7-nitro-5-phenyl-2H-1,4-benzodiazepin-2-one, 7-chloro-1,3-dihydro-1-methyl-5-phenyl-2H-1,4-benzodiazepin-2-one, 5-(2-flurophenyl)-1,3-dihydro-1-methyl-7-nitro-2H-1,4-benzodiazepin-2-one, 7-chloro-1,3-dihydro-3-hydroxy-5-phenyl-2H-1,4-benzodiazepin-2-one, 3-hydroxopregane-11,20-dione, 5,5-diethylbarbituric acid, 5-ethyl-5-(1-methylbutyl)barbituric acid, 5-ethyl-5-phenylbarbituric acid, and their salts.

34. The method of claim 1, wherein said receptor is at least one selected from the group consisting of $GABA_A$ receptors and glycine-strychnine sensitive receptors.

* * * * *